United States Patent [19]

Hauri et al.

[11] 4,403,960
[45] Sep. 13, 1983

[54] EXTRACORONAL HOLDING MEMBER FOR DENTAL PROSTHESES

[76] Inventors: Robert Hauri, Bahnhofstrasse 33, Aarau; Peter Reinhard, Weingartenstrasse 8, Spreitenbach, both of Switzerland

[21] Appl. No.: 357,274

[22] Filed: Mar. 11, 1982

[30] Foreign Application Priority Data

Jun. 18, 1981 [CH] Switzerland .................. 4043/81

[51] Int. Cl.³ ............................................. A61C 13/22
[52] U.S. Cl. .................................................. 433/177
[58] Field of Search ............... 24/201 C, 217 W, 218, 24/241 S; 433/173, 176, 177, 174

[56] References Cited

U.S. PATENT DOCUMENTS 1,434,245 10/1922 Choate ................................. 24/218
2,916,787 12/1959 Samiran ............................... 24/218
4,085,506 4/1978 Lew ..................................... 433/173

FOREIGN PATENT DOCUMENTS 343061 6/1960 Switzerland .

Primary Examiner—Robert Peshock
Attorney, Agent, or Firm—Roylance, Abrams, Berdo & Farley

[57] ABSTRACT

A holding member assembly comprises a shell-like female part with an annular cavity and a male part with a torus adapted to mate with the cavity. The torus contains a slot with an annular spring which, on insertion of the male into the female, engage in a holding slot of the female part. The female part is embedded into a tooth crown, whereas the male part is connected to a dental prosthesis part. Through constructing the female part with the cavity, it is possible to produce holding members with reduced overall height compared with the known holding members, but which still have an excellent stability.

20 Claims, 5 Drawing Figures

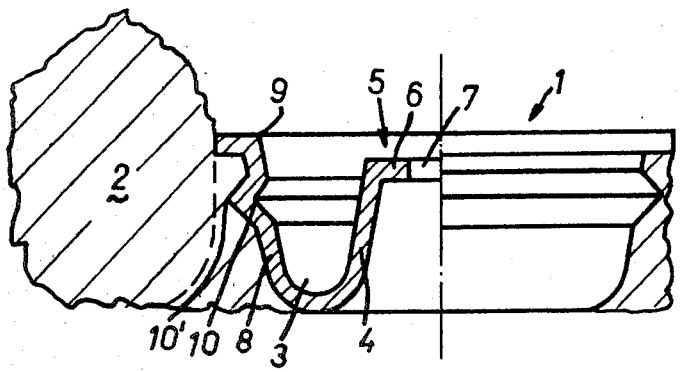
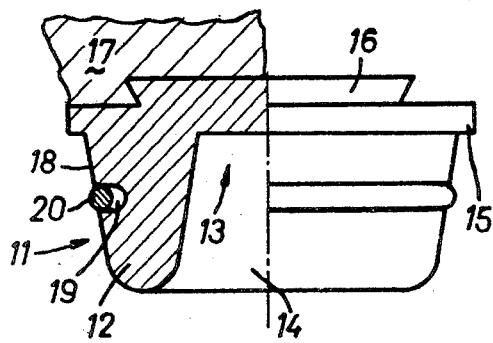
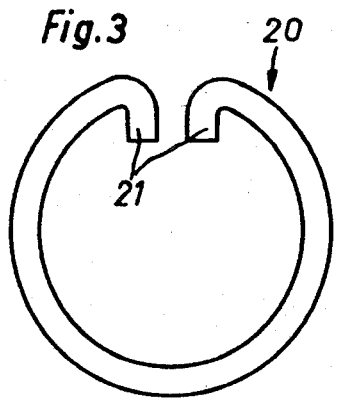
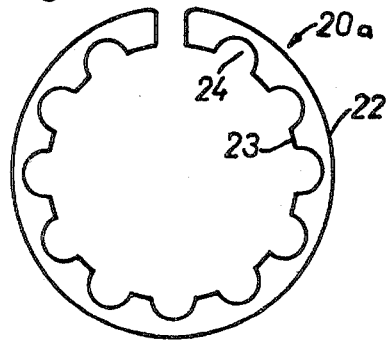
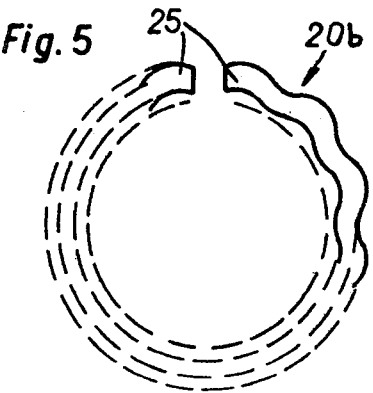

EXTRACORONAL HOLDING MEMBER FOR DENTAL PROSTHESES

This invention relates to an extracoronal holding member for dental prostheses and especially to such an article which is in two parts, namely a male part and a female part, with the parts being held together by an annular spring when the dental prosthesis is inserted.

BACKGROUND OF THE INVENTION

Increasing use is being made of the possibility of the wearers of dental prostheses being able to detach the prosthesis from its anchoring themselves and remove it, e.g., for cleaning purposes. To this end, an attaching member is known (Swiss Pat. No. 343,061) comprising a cap-like member, which includes two screwed-together portions forming an assembly called the female part and a cooperating member also formed by two screwed-together portions and called the male part. The male and female parts are held together without clearance by an annular spring or circular clip. Both for releasing and attaching the dental prosthesis, the annular spring or clip is elastically widened at its holding surface provided on the male part, so that there is a certain resistance when releasing and attaching the dental prosthesis.

However, it is a disadvantage of the known holding member that it has a relatively large overall height due to the two spaced, superimposed guidance surfaces necessary for obtaining adequate stability of the hold member. Due to the relatively large number of individual components of this known hold member, it is also complicated in construction and therefore expensive.

BRIEF SUMMARY OF THE INVENTION

An object of the present invention is to provide a holding member of the aforementioned type in which its construction can be considerably simplified and its overall height made considerably less than that of the known devices without loss of stability.

Briefly described, the invention includes a holding member assembly for dental prostheses comprising a female member having means defining a generally annular cavity therein, a male member having a generally toroidal portion shaped and dimensioned to be closely received in said female member, an annular spring for releasably holding said members together and means for securing one of said members to at least one tooth of a wearer and the other of said members to a prosthesis.

Thus, the shortcomings of the prior art are overcome by a structure in which the female part is provided with an annular cavity and the male member is shaped as a ring for insertion in the annular cavity. Thus, the male part is supported on faces of the female part which are relatively remote from the central axis of the holding member assembly, thereby ensuring a high degree of stability of the assembly, accompanied by significantly reduced overall height.

In order that the manner in which the foregoing and other objects are attained in accordance with the present invention can be understood in detail, particularly advantageous embodiments thereof will be described with reference to the accompanying drawings, which form a part of this specification, and wherein:

FIG. 1 is a partly schematic side elevation, partly in section, of the female portion of a device in accordance with the invention;

FIG. 2 is a partly schematic side elevation, partly in section, of the male portion of a prosthesis-holding device in accordance with the invention for use with the device of FIG. 1;

FIG. 3 is plan view of an annular spring for use with the device of FIG. 2; and

FIGS. 4 and 5 are plan views of further embodiments of annular springs usable with the device of FIG. 2.

DETAILED DESCRIPTION OF THE PREFERRED EMBODIMENTS

Figure 6:
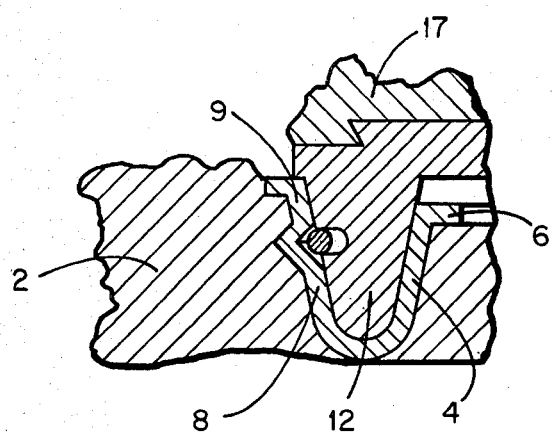
FIG. 6 illustrates the male and female members when coupled.

As previously indicated, the device of the present invention is formed in two cooperating parts, a female part and a male part which interfit but which are shown separately in the figures.

The female part 1 shown in FIG. 1 is molded in a conventional manner, not further described, onto a schematically indicated tooth corona or crown 2. Female part 1 is constructed as a hollow shell and has an annular cavity 3 forming a closed (i.e., endless) channel. The inner wall 4 of cavity 3 forms a central projection 5 bounded by a cover 6 in which a central rinsing opening 7 is provided. The outer wall 8 of the female part extends upwardly higher than the cover 6 of central projection 5 and has at its end an outwardly extending flange 9 which reinforces outer wall 8. On the outer side of cavity 3, outer wall 8 has a holding slot 10 corresponding to an outwarly protruding rib 10 which functions as an anchoring means on the outside of outer wall 8.

The male part 11 shown in FIG. 2 is constructed as a torus 12 having a central recess 14. A wall or base 13 extends across one side of torus 12, closing that side of the recess. Base 13 has a radially outwardly extending flange 15 projecting beyond torus 12 and is provided on its top face with an anchoring plate 16, having shoulders with inclined sides which permit perfect anchoring with a dental prosthesis part schematically illustrated at 17.

In order that the male part 11 can be inserted without clearance into female part 1, torus 12 has the same cross-sectional shape as cavity 3 of female part 1. A circumferential slot 19 is formed approximately in the center of outer wall 18 of torus 12 and receives an annular spring 20. As is illustrated in FIGS. 3 to 5, different contructions of annular spring 20 are possible.

When male part 11 is inserted into female part 1, annular spring 20 is initially somewhat compressed and then engages in the holding slot 10. By using corresponding construction on the sloping slot walls and because of the arrangement of slot 10, it is possible to ensure that annular spring 20 holds the male part in clearance-free manner in cavity 3 of the female part.

Due to the fact that annular spring 20 is mounted in male part 11, it is removed at the time of removing dental prosthesis part 17 and the male part from female part 1 and hold slot 10 consequently becomes accessible, e.g., for cleaning. To ensure that the bristles of the brush used for cleaning do not stick to the annular spring ends and consequently tear the spring 20 out of slot 19, those ends are constructed in accordance with FIGS. 3 to 5.

In FIG. 3, annular spring 20 is a bent wire, round in cross-section, whose ends 21 are bent inwardly. Holding slot 10 in female part 1 has corresponding depressions, not shown, into which ends 21 project. Annular spring 20a in FIG. 4 is constructed as a flat ring with a smooth outer edge 22. Inner edge 23 has a plurality of recesses 24 which form areas or points having increased flexibility and elasticity. Annular spring 20b in FIG. 5 is made from a round wire and is shaped in indulating manner, its ends 25 being appropriately bent inwardly.

As can be gathered from FIG. 1, walls 4 and 8 of female part 1 conically converge towards the bottom of cavity 3. Therefore, torus 12 of male part 11 also has a conical shape. However, cavity 3 and torus 12 need not be conical, e.g., the walls could be approximately parallel. If the walls slope, the slope should only be sufficiently great to ensure perfect supporting of male part 11 in female part 1 by annular spring 20.

The construction of the holding member assembly formed from female part 1 and male part 11 is extremely simple. The essential point is that no screwed-together parts need be used. Despite the extremely limited overall height, very good stability of the holding member is obtained.

In FIGS. 1 and 2, the two parts are shown on a greatly increased scale. In reality, the greatest diameter of female part 1 is approximately 5 mm, while the overall height of female part 1 and male part 11 is approximately 2.5 mm, i.e., only about half that of known holding members.

With limited adaptation, the previously described extracoronal holding member can so be used as an intracoronal holding member. The uses of the known holding members also exist in the present case. Thus, the holding member can be arranged in a plastic web for holding purposes. The gold construction for soldering to a tooth root is also possible. It can also be used as an intracoronal insert, i.e., the male part and female part are inserted into the tooth. Gold, platinum and alloys thereof are used as materials for the hold member.

While certain advantageous embodiments have been chosen to illustrate the invention, it will be understood by those skilled in the art that various changes and modifications can be made in accordance with the invention as defined in the appended claims.

What is claimed is:

1. A holding member assembly for dental prostheses, comprising
    a female member having an inner wall and an outer wall coupled by a bottom member defining a generally annular cavity therebetween, said outer wall having a radially outwardly extending flange reinforcing said female member;
    a male member having a generally toroidal portion shaped and dimensioned to be closely received in said female member cavity;
    an annular spring for releasably holding said members together;
    means, in said cavity, for receiving said spring; and
    means for securing one of said members to at least one tooth of a wearer and the other of said members to a prosthesis;
    whereby the assembly securely couples a prosthesis to a tooth, is stable and has a reduced overall height.

2. An assembly according to claim 1 wherein said outer wall has a reinforcing rib on an outer surface thereof.

3. An assembly according to claim 2 wherein said cavity in said female part and said toroidal portion of said male part are conical in cross-sectional shape.

4. An assembly according to claim 1 wherein inner wall has a radially inwardly extending flange reinforcing said female member.

5. As assembly according to claim 4 wherein said radially inwardly extending flange has an opening therethrough.

6. An assembly according to claim 1 wherein said inner wall is shorter than said outer wall.

7. An assembly according to claim 1 wherein said female member comprises a holding slot for receiving said annular spring; and said annular spring is supported on said male member.

8. An assembly according to claim 7, wherein the ends of said annular spring are bent inwardly.

9. A holding member according to claim 7, wherein said annular spring includes means defining recesses on the inner edge thereof forming points of greater elasticity.

10. An assembly according to claim 7, wherein said annular spring has an undulating configuration and inwardly bent ends.

11. An assembly according to claim 7 wherein said holding slot is defined by opposing frustoconical walls.

12. An assembly according to claim 1 wherein said female member is secured to at least one tooth of a wearer and said male member is secured to a prosthesis.

13. A holding member assembly for dental prostheses, comprising
    a female member having an inner wall and an outer wall coupled by a bottom member defining a generally annular cavity therebetween, said inner wall having a radially inwardly extending flange reinforcing said female member;
    a male member having a generally toroidal portion shaped and dimensioned to be closely received in said female member cavity;
    an annular spring for releasably holding said members together;
    means, in said cavity, for receiving said spring; and
    means for securing one of said members to at least one tooth of a wearer and the other of said members to a prosthesis;
    whereby, the assembly securely couples a prosthesis to a tooth, is stable and has a reduced overall height.

14. An assembly according to claim 13 wherein said outer wall has a reinforcing rib on an outer surface thereof.

15. An assembly according to claim 14 wherein said cavity in said female part and said toroidal portion of said male part are conical in cross-sectional configuration.

16. An assembly according to claim 13 wherein said radially inwardly extending flange has an opening therethrough.

17. An assembly according to claim 13 wherein said inner wall is shorter than said outer wall.

18. An assembly according to claim 13 wherein said female member comprises a holding slot for receiving said annular spring; and said annular spring is supported on said male member.

19. An assembly according to claim 18 wherein said holding slot is defined by opposing frustoconical walls.

20. An assembly according to claim 13 wherein said female member is secured to at least one tooth of a wearer and said male member is secured to a prosthesis.

* * * * *